United States Patent [19]

Maas et al.

[11] 4,326,091
[45] Apr. 20, 1982

[54] PROCESS FOR THE SELECTIVE ADSORPTION OF PARA-XYLENE

[75] Inventors: Rudolf J. Maas; Rene M. Visser, both of Amsterdam, Netherlands

[73] Assignee: Shell Oil Company, Houston, Tex.

[21] Appl. No.: 143,386

[22] Filed: Apr. 24, 1980

[30] Foreign Application Priority Data

May 1, 1979 [GB] United Kingdom ............... 15081/79

[51] Int. Cl.³ .......................... C07C 7/13; C10G 25/03
[52] U.S. Cl. .................................................... 585/828
[58] Field of Search .................... 585/828; 208/310 Z

[56] References Cited

U.S. PATENT DOCUMENTS

| | | | |
|---|---|---|---|
| 3,686,343 | 8/1972 | Bearden, Jr. et al. | 585/828 |
| 3,732,325 | 5/1973 | Pharis et al. | 585/828 |
| 3,793,385 | 2/1974 | Bond et al. | 585/478 |
| 3,813,452 | 5/1974 | Bieser | 585/479 |
| 4,108,915 | 8/1978 | Rosback et al. | 585/828 |

*Primary Examiner*—Delbert E. Gantz
*Assistant Examiner*—William Leader

[57] ABSTRACT

A process for preparing a stream enriched in para-xylene from a mixture of para-xylene with other aromatic hydrocarbons which comprises contacting the mixture with a particular modified crystalline silicate and subsequently desorbing the para-xylene enriched stream from the silicate.

12 Claims, No Drawings

PROCESS FOR THE SELECTIVE ADSORPTION OF PARA-XYLENE

FIELD OF THE INVENTION

This invention relates to a process for producing a stream rich in para-xylene from a mixture consisting substantially of aromatic hydrocarbons with six to nine carbon atoms in the molecule and including at least some para-xylene and some ethyl benzene by contacting the mixture with a modified crystalline silicate and subsequently desorbing a para-xylene enriched stream from the silicate.

BACKGROUND OF THE INVENTION

Para-xylene is an important base material in the chemical industry. It is generally required substantially free from other aromatic hydrocarbons and in particular from the isomeric compounds, ortho-xylene, meta-xylene, and ethylbenzene often produced during its manufacture. Since the four isomeric compunds closely resemble each other as regards their physical and chemical properties, the separation of para-xylene from such a mixture presents a particular problem.

While it is known from U.S. Pat. No. 3,729,523 to use crystalline silicates for the separation of para-xylene from the said mixtures, in practice a large quantity of ethyl benzene is also adsorbed by the silicate. The present invention seeks to improve the selectivity of the crystalline silicate for para-xylene over ethyl benzene.

It has now been found that the selectivity for para-xylene over ethyl benzene can be improved by using a modified crystalline silicate.

SUMMARY OF THE INVENTION

In a process for selectively adsorbing para-xylene from a mixture of aromatic hydrocarbons of six to nine carbon atoms including para-xylene and ethyl benzene utilizing a crystalline silicate, the adsorption selectivity of para-xylene over ethyl benzene is improved by modifying the siicate by bringing it into contact with a solution of concentration m (in gion/l) of a salt of a polyvalent cation of charge density (e/r) (in $nm^{-1}$) wherein (e/r)m is at least 45 after which it is filtered, washed and dried at an elevated temperature so that the salt decomposes to leave the metal cation in the crystalline silicate. After contacting the silicate with the mixture a stream rich in para-xylene over ethylbenzene is desorbed from the silicate.

DESCRIPTION OF THE PREFERRED EMBODIMENT

Crystalline silicates are characterized as a class of compounds by their thermal stability, their crystallinity which follows from the fact that they all show a clear X-ray powder diffraction pattern, their adsorption behavior, and their overall composition.

In this specification the term crystalline silicate will be used to refer to crystalline silicates which after calcining for one hour in air at 500° C. display the following characteristics:

(a) They are thermally stable up to at least 600° C. In this specification, "thermally stable up to t°C." shall mean that after heating the crystalline silicate to t°C. its X-ray powder diffraction pattern is not changed.

(b) They have an X-ray powder diffraction pattern showing iner alia the reflections given in Table A below.

TABLE A

| Source Cu-Kα 2θ | Wave length 0.15418nm Relative intensity |
|---|---|
| 7.9–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M |

In which the letters have the following significance:
VS = very strong;
S = strong;
M = moderate;
W = weak.
Q is the angle according to Bragg's law.

(c) In their so-called "H-form" after evacuation to $2 \times 10^{-9}$ bar at a temperature of 400° C. for 16 hours and measured at a hydrocarbon pressure of $8 \times 10^{-2}$ bar at a temperature of 100° C. they have an adsorption of n-hexane (n-$C_6$) of at least 0.8 mmol/g and an adsorption of 2,2 dimethyl butane (2,2 DMB) of at least 0.5 mmol/g, and the ratio $$\frac{\text{adsorption of n-hexane}}{\text{adsorption of 2,2 dimethylbutene}}$$

should be at least 1.5.

(d) Their chemical formula is:

$$y(1.0 \pm 0.3)M_2O \cdot y(aFe_2O_3 \cdot bAl_2O_3) \cdot SiO_2$$

Where:
M is H and an alkali metal
a+b=1;
a≧0;
b≧0
0≦y≦0.1

For the adsorption measurements under paragraph (c) the silicate must be in its so-called "H-form" as described below.

A modified crystalline silicate shall mean a crystalline silicate which has been brought into contact with solution of a salt of a polyvalent metal cation, filtered, washed and dried or calcined preferably at between 400° C. and 600° C., so that the salt decomposes leaving the metal cation in the silicate. The solution is conveniently, though not necessarily an aqueous solution.

The salt conveniently can be one of an organic acid such as a formate or an oxalate, which readily decomposes on heating, or alternatively of an inorganic acid, such as a nitrate which also decomposes without leaving traces of undesirable compounds or elements in the modified crystalline silicate.

In order to obtain the increase in the selectivity for para-xylene over ethyl benzene in accordance with the invention, the cation should have such a charge density (being the quotient of the charge e and the ion radius R) in $nm^{-1}$ and a concentration m in gion/l that the product of the charge density and the concentration amounts to at least 45. Compared with conventional processes, application of the present invention yields a desorbate which is richer in para-xylene, which may in some cases obviate the need for further purification steps, or certainly render any such steps, for example crystallisation, more efficient.

Where the valency of the metal cation is 2, $(e/R)m$ is preferably in excess of 60 in order to obtain a significant increase in the selectivity for para-xylene to ethyl benzene $S_{PX/EB}$. At values of $(e/R)m$ in excess of 100 a 50 percent increase in the selectivity $S_{PX/EB}$ can be obtained at a temperature of 80° C.

While the invention produces a valuable increase in the selectivity $S_{PX/EB}$ where metal cations of a valency of two are employed, a still greater improvement can be obtained where the metal cation has a valency of three. In this case, an improvement in the selectivity $S_{PX/EB}$ of 20 percent is obtained where $(e/R)m$ is greater than 45 and as much as 100 percent improvement when $(e/R)m$ is greater than 115 at a temperature of 80° C.

At lower temperatures, for example, in the liquid phase a selectivity $S_{PX/EB}$ in excess of five may be found. These values have been established with respect to a silicate in the Na-form.

However, while such increases in the selectivity $S_{PX/EB}$ are very encouraging, it has been found that a pretreatment of the crystalline silicate can still further increase its selectivity. Such a pretreatment involves substitution of hydrogen ions for M ions present in the originally prepared and calcined silicate, which are often sodium ions. (Such a silicate is said to be in the "H-form"). This may conveniently be performed by bringing the crystals into contact with an ammonium salt, or a weak acid. The crystals are then washed and dried. Where an ammonium salt is used they are also heated until the ammonium has decomposed to leave hydrogen ions in the crystal structure. While this pretreatment will in itself increase the selectivity for para-xylene, its combination with the modification in accordance with the invention, whereby a metal cation is fixed in the crystalline structure, produces a substantial further improvement in the desired selectivity of some 10 percent in the case of a crystalline aluminum silicate with a low Al content to more than 70 percent for a crystalline iron silicate with a high Fe content.

For modifying the crystalline silicate, suitable metal cations may be selected from the alkaline earth metals, rare earth metals, the iron group, manganese, aluminum and gallium. Of these magnesium and calcium, are preferred, and iron, aluminum and lanthanum are most preferred.

The salt of the metal cation should decompose on heating to leave only the metal cation in the crystalline silicate. Particularly suitable salts are nitrates and oxalates which decompose without depositing any side products which might adversely influence the performance of the crystalline silicate.

Best results are found when the solution of the salt is made as concentrated as possible, say from a two molar solution to one of the maximum solubility of the salt in question.

The unmodified and untreated crystalline silicate preferably has an X-ray diffraction pattern substantially as set out in Table B below:

TABLE B

| Source Cu—Kα 2θ | Relative intensity (100 . I/I$_o$) | Wave length 0.15418nm description of the reflection |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100* | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

*I$_o$ = intensity of the strongest separated reflection occurring in the pattern.
The abbreviations used in Table B to describe the reflections have the following meanings:
SP = sharp;
SR = shoulder;
NL = normal;
BD = broad.
θ is the angle according to Bragg's law.

The pores of the crystalline silicate are generally substantially elliptical in shape and their diameter is between 5 and 6 Å.

In general terms this invention defines a process for preparing a stream enriched in para-xylene from a mixture consisting substantially of aromatic hydrocarbons with six to nine carbon atoms in the molecule including para-xylene and ethyl benzene which process comprises contacting the mixture with the crystalline silicate described herein which selectively adsorbs the para-xylene and subsequently desorbing the para-xylene enriched stream from the silicate. The para-xylene enriched stream may be desorbed from the silicate by any of several alternative procedures. Thus, heating the silicate, reducing the partial pressure of the sorbed material in the vapor or liquid surrounding the silicate, lowering the total pressure of the system or purging with a suitable inert gas or liquid effect suitable desorption of the para-xylene enriched stream.

The invention will now be further described by way of example. First the preparation of a number of candidate crystalline silicates will be described:

Silicate A

A crystalline silicate was prepared from a mixture of Fe(NO$_3$)$_3$, SiO$_2$, NaOH and [(C$_3$H$_7$)$_4$]OH in water with a molar composition as follows:

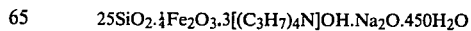

25SiO$_2$.¼Fe$_2$O$_3$.3[(C$_3$H$_7$)$_4$N]OH.Na$_2$O.450H$_2$O

The mixture was heated to 150° C. in an autoclave under autogeneous pressure, at which temperature it was maintained for 24 hours after which it was filtered and washed until its pH was approximately eight. After drying the resulting crystals were calcined for eight hours at 500° C. This crystalline iron silicate will be referred to as Silicate A.

(a) Silicate A was thermally stable to above 600° C.

(b) It had an X-ray powder diffraction pattern showing the reflections given in Table B above.

(c) In the "H-form" at 100° C. it has an adsorption of n-$C_6$ of 1.22 mmol/g and of 2,2 DMB of 0.60 mmol/g.

(d) Its chemical formula was $$0.011Na_2O.0.011(0.97Fe_2O_3.0.03Al_2O_3).SiO_2.$$

The occurrence of $Al_2O_3$ in the formula can be explained by the presence of up to 500 ppm Al in the $SiO_2$ used in its preparation. Up to 240 ppm Al is also found in the $Fe(NO_3)_3$ used.

Silicate B

Silicate A was contacted with a 1 molar $NH_4NO_3$ solution at 100° C. for 10 hours (2×5 hr). The crystals were filtered, washed and then dried for 15 hours at 120° C. This treated crystalline iron silicate will be referred to as Silicate B.

Silicate C

Silicate A was contacted with a 4 molar solution of $La(NO_3)_3$ at 100° C. for 10 hours (2×5 hr). The crystals were filtered, washed and then dried at 400° C. for 15 hours. This modified crystalline iron silicate will be referred to as Silicate C.

Silicate D

Silicate B was contacted with a 4 molar solution of $La(NO_3)_3$ at 100° C. for 10 hours (2×5 hr). The crystals were filtered, washed and then dried at 400° C. for 15 hours. This modified crystalline iron silicate will be referred to as Silicate D.

Silicate E

A reaction mixture was prepared from $SiO_2$, $NaNO_3$ and $[(C_3H_7)_4N]OH$ in water with a molar composition as follows:

$$29.1SiO_2.3.0[(C_3H_7)_4N]OH.1Na_2O.430H_2O$$

The mixture was heated to 150° C. in an autoclave under autogenous pressure, for 24 hours, then filtered and washed until its pH was below 9. After drying at 120° C., the crystals were calcined at 500° C. for three hours. This crystalline silicate (a) was thermally stable to above 600° C.;

(b) had an X-ray powder diffraction pattern showing inter alia the reflections given in Table B above;

(c) in the H-form at 100° C. it has an adsorption of n-$C_6$ of 1.29 mmol/g and of 2,2 DMB of 0.67 mmol/g;

(d) its chemical formula was $$0.0003Na_2O.0.0003Al_2O_3.SiO_2.$$

The occurrence of $Al_2O_3$ in the final formula can be explained by the presence of up to 500 ppm Al in the $SiO_2$ used in its preparation. It was then contacted with a 1 molar solution of $NH_4NO_3$ for two hours (2×1 hr) at 100° C. which was followed by drying and at 120° C. for 15 hours. This crystalline silicate will be referred to as Silicate E.

Silicate F

Silicate E was contacted with a 1 molar solution of $RbNO_3$ for 10 hours (2×5 hrs) at 100° C. The crystals were filtered and washed before drying for 15 hours at 400° C. This modified crystalline silicate will be referred to as Silicate F.

Silicate G

Silicate E was contacted with a 1 molar solution of $La(NO_3)_3$ for 10 hours (2×5 hrs) at 100° C. After filtering and washing it was dried for 15 hours at 400° C. This modified crystalline silicate will be referred to as Silicate G.

Silicate H

Silicate E was contacted with a 4 molar solution of $La(NO_3)_3$ for 10 hours (2×5 hrs) at 100° C. After filtering and washing it was dried for 14 hours at 400° C. This modified crystalline silicate will be referred to as Silicate H.

Silicate I

Silicate B was contacted with a 4 molar solution of $Ca(NO_3)_2$ for 10 hours (2×5 hrs) at 100° C. After filtering and washing it was dried for 15 hours at 400° C. This modified crystalline silicate will be referred to as Silicate I.

Silicate J

Silicate B was contacted with a 2.5 molar solution of $Ca(NO_3)_2$ for 10 hours (2×5 hrs) at 100° C. After filtering and washing, it was dried for 15 hours at 400° C. This modified crystalline silicate will be referred to as Silicate J.

Silicate K

A crystalline silicate was prepared from a mixture of $Al(NO_3)_3$, $SiO_2$, NaOH and $[(C_3H_7)_4N]OH$ in water with a solar composition as follows:

$$25SiO_2.\tfrac{1}{4}Al_2O_3.3[(C_3H_7)_4N]OH.Na_2O.450H_2O$$

The mixture was heated to 150° C. in a autoclave under autogenous pressure, at which temperature it was maintained for 24 hours after which it was filtered and washed until its pH was approximately 8. The resulting crystalline silicate after drying and calcining at 500° C. for three hours will be referred to as Silicate K.

(a) Silicate K was thermally stable to above 600° C.;

(b) It had an X-ray powder diffraction pattern showing the reflections given in Table B above.

(c) In the H-form its adsorption of n-$C_6$ was 1.25 mmol/g and that of 2,2 DMB was 0.62 mmol/g.

(d) Its chemical formula was 0.006 $Na_2O.0.006Al_2O_3.SiO_2$.

Silicate L

Silicate K was contacted with a 1 molar $NH_4NO_3$ solution at 100° C. for 10 hours (2×5 hrs). The crystals were filtered, washed and then dried for 15 hours at 120° C. This treated silicate will be referred to as Silicate L.

Silicate M

Silicate L was contacted with a 0.8 molar $Mg(NO_3)_2$ solution at 100° C. for 10 hours (2×5 hrs). The crystals were filtered and washed and then dried at 400° C. for 15 hours. This modified crystalline silicate will be referred to as Silicate M.

Silicate N

Silicate L was contacted with a 2.5 molar $Mg(NO_3)_2$ solution at 100° C. for 10 hours (2×5 hrs). The crystals were filtered and washed and then dried at 400° C. for 15 hours. This modified crystalline silicate will be referred to as Silicate N.

Silicate O

Silicate L was contacted with a 1 molar $Fe(NO_3)_3$ solution at 100° C. for 10 hours (2×5 hrs). The crystals were filtered and washed and then dried at 400° C. for 15 hours. This modified crystalline silicate will be referred to as Silicate O.

Silicate P

Silicate L was contacted with a 6 molar $Ca(NO_3)_2$ solution at 100° C. for 10 hours (2×5 hrs). The crystals were filtered and washed and then dried at 400° C. for 15 hours. This modified crystalline silicate will be referred to as Silicate P.

Silicate Q

A crystalline silicate was prepared from a mixture of $Al(NO_3)_3$, $Fe(NO_3)_3$, $SiO_2$, NaOH and $[(C_3H_7)_4N]OH$ in water with a molar composition as follows:

$$25SiO_2.5/64Fe_2O_3.3/64Al_2O_3.3.0[(C_3H_7)_4N]OH.Na_2O.450H_2O.$$

The mixture was heated to 150° C. in an autoclave under autogenous pressure, at which temperature it was maintained for 24 hours after which it was filtered and washed until the pH was 8. After drying the resulting crystals were calcined for eight hours at 500° C. This crystalline silicate will be referred to as Silicate Q.

(a) Silicate Q was thermally stable to above 600° C.

(b) It had an X-ray powder diffraction pattern showing the reflections given in Table B above.

(c) In the H-form its adsorption of $n-C_6$ was 1.27 mmol/g and that of 2,2 DMB was 0.63 mmol/g.

(d) Its chemical formula was $$0.0044Na_2O.0.0044(0.64Fe_2O_3.0.34Al_2O_3).SiO_2.$$

Silicate R

Silicate Q was contacted with a 1 molar $La(NO_3)_3$ solution at 100° C. for 10 hours (2×5 hrs). The crystals were filtered and washed and then dried at 400° C. for 15 hours. This modified crystalline silicate will be referred to as Silicate R.

Silicate S

Silicate Q was contacted with a 4 molar $La(NO_3)_3$ solution at 100° C. for 10 hours (2×5 hrs). The crystals were filtered and washed and then dried at 400° C. for 15 hours. This modified crystalline silicate will be referred to as Silicate S.

EXAMPLE I

Samples of 100 g of each of Silicates A to H inclusive, J and L to O inclusive were brought into contact with a nitrogen stream at 80° C. containing para-xylene and ethyl benzene in equal molar proportions, the $C_8$ aromatics having a combined partial pressure of 45 m bar. After equilibrium was reached the samples were weighed, and the ratio of para-xylene to ethyl benzene established.

The following results were obtained.

| Silicate | $\left(\dfrac{e}{R}\right) m$ | Para-xylene and ethyl benzene absorbed (% w) | Ratio PX/EB |
|---|---|---|---|
| A | — | 8.1 | 0.8 |
| B | — | 9.5 | 1.7 |
| C | 118 | 8.3 | 1.3 |
| D | 118 | 10.8 | 3.4 |
| E | — | 8.9 | 1.2 |
| F | 7 | 9.5 | 1.0 |
| G | 30 | 9.5 | 1.3 |
| H | 118 | 10.5 | 2.4 |
| J | 51 | 10.0 | 1.9 |
| L | — | 9.5 | 1.5 |
| M | 24 | 9.5 | 1.4 |
| N | 76 | 10.1 | 1.9 |
| O | 47 | 10.1 | 2.0 |

Note:
"Ratio PX/EB" is the ratio of para-xylene adsorbed to ethyl benzene adsorbed. In the case where the composition of the gas stream remains constant and the quantities of para-xylene and ethyl benzene in the stream are equal the ratio PX/EB is equivalent to the selectivity $S_{PX/EB}$ for para-xylene over ethyl benzene for the crystalline silicate.

Commentary

Comparing Silicate C to Silicate A it will be seen, that the modification of Silicate C in accordance with the invention has improved the ratio PX/EB substantially. Similarly, taking Silicate D a similar improvement over Silicate B is demonstrated. Where the product (e/R)m is smaller the effect is less marked, as with Silicate J, although still useful.

Taking Silicate E it is seen that the modifications resulting in Silicates F and G do not lead to any marked improvement-the product (e/R)m is too small, and in the case of Silicate F, Rb is monovalent. Silicate H in accordance with the invention, however, shows a significant improvement.

Starting from Silicate L, Silicates N and O, which are in accordance with the invention show a significant improvement, whereas Silicate M[(e/R)m=24] does not.

EXAMPLE II

Samples of 100 g of each of Silicates A, B, D, I, J, L, and N to S inclusive were brought separately into contact with a solution of 2,2,4-trimethylpentane at 25° C. containing 4% w of para-xylene and ethyl benzene in a ratio of para-xylene to ethyl benzene of 1. After equilibrium was reached the solution was analyzed and the ratio of para-xylene to ethyl benzene adsorbed by the samples thus established. The following results were obtained.

| Silicate | $\dfrac{e}{R} \times m$ | Liquid-solids ratio | Para-xylene and ethyl benzene adsorbed (% w) | Ratio PX/EB | $S_{PX/EB}$ |
|---|---|---|---|---|---|
| A | — | 10.0 | 10.3 | 2.7 | 3.7 |
| B | — | 10.1 | 10.4 | 3.7 | 5.7 |
| D | 118 | 13.0 | 11.8 | 5.6 | 9.0 |
| I | 81 | 11.8 | 10.6 | 5.2 | 7.8 |
| J | 51 | 10.2 | 10.9 | 4.2 | 6.6 |
| L | — | 10.2 | 10.3 | 3.5 | 5.1 |
| N | 76 | 10.3 | 10.7 | 4.2 | 6.3 |
| O | 47 | 10.5 | 10.6 | 4.0 | 6.3 |
| P | 121 | 9.8 | 11.2 | 4.6 | 7.3 |
| Q | — | 10.0 | 9.3 | 2.7 | 3.5 |

-continued

| Silicate | $\frac{e}{R} \times m$ | Liquid-solids ratio | Para-xylene and ethyl benzene adsorbed (% w) | Ratio PX/EB | $S_{PX/EB}$ |
|---|---|---|---|---|---|
| R | 30 | 10.0 | 9.4 | 2.7 | 3.6 |
| S | 118 | 10.2 | 11.0 | 5.1 | 7.0 |

Note:
"Ratio PX/EB" is the ratio of para-xylene adsorbed to ethyl benzene adsorbed.
"$S_{PX/EB}$" is the selectivity for para-xylene over ethyl benzene taking account of the reduced proportion of para-xylene in the solution under equilibrium conditions, i.e.;
$$S_{PX/EB} = \frac{PX/EB \text{ in the absorbed phase}}{PX/EB \text{ in the liquid phase}}$$

Commentary

A substantial improvement is found in the selectivity $S_{PX/EB}$ for Silicate D, I, and J over Silicates A and B from which they were derived. Similarly, Silicates N, O, and P showed an improvement over Silicate L. Moreover, Silicate R [(e/R)m=30] showed hardly any increase over Silicate Q whereas Silicate S [(e/R)m=118] showed a marked increase. It should be noted that Silicates D, I, J, N, O, P, and S are in accordance with the invention.

What is claimed is:

1. A process for preparing a stream enriched in para-xylene from a mixture consisting substantially of aromatic hydrocarbons with six to nine carbon atoms in the molecule including para-xylene and ethyl benzene, comprising contacting the mixture with a crystalline silicate as selective adsorbent of para-xylene, and subsequently desorbing the para-xylene enriched stream from the silicate, which crystalline silicate, after calcining in air at 500° C., (a) is thermally stable up to at least 600° C.,
   (b) has an X-ray diffraction pattern (Cu-Kα radiation, 0.15418 nm wave length) showing at least the reflections below:

| $2\theta$ | Relative intensity |
|---|---|
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | where $\theta$ is the Bragg angle, VS = very strong, S = strong, M = moderate, W = weak.

(c) measured at a hydrocarbon pressure of $8 \times 10^{-2}$ bar at a temperature of 100° C. in the H-form it has an adsorption of n-hexane (n-C$_6$) of at least 0.8 mmol/g and an adsorption of 2,2-dimethylbutane (2,2-DMB) of at least 0.5 mmol/g, and the ratio $$\frac{\text{adsorption of n-hexane}}{\text{adsorption of 2,2-dimethylbutane}}$$

should be at least 1.5, (d) has the following overall composition:

$$y(1.0 \pm 0.3)M_2O \cdot y(aFe_2O_3 \cdot bAl_2O_3) \cdot SiO_2$$

where:
M is H and an alkali metal
a+b=1
a≥0
b≥0
0≤y≤0.1 characterized in that the crystalline silicate is modified in order to increase its selectivity for para-xylene by bringing it into contact for a period of about 10 hours with a solution of concentration m (in gion/l) of a salt of a polyvalent rare earth cation whose charge density is e/R (in nm$^{-1}$) wherein the product (e/R)m is at least 45, after which it is filtered, washed and dried at an elevated temperature so that the salt decomposes to leave the metal cation in the crystalline silicate.

2. A process as claimed in claim 1, in which the solution of the salt of the polyvalent metal cation is an aqueous solution.

3. A process as claimed in claim 1, in which the metal cation has a valency of 2 or 3.

4. A process as claimed in claim 3 in which the metal cation has a valency of 2 and that the said product is at least 100.

5. A process as claimed in claim 3 in which the metal cation has a valency of 3 and that the said product in at least 80.

6. A process as claimed in claim 5 in which the said product is at least 115.

7. A process as claimed in claim 1, 2, 3, 4, 5, or 6 in which the metal cation is lanthanum.

8. A process as claimed in claim 1, 2, 3, 4, 5, or 6 in which the salt is a salt of an organic acid.

9. A process as claimed in claim 1, 2, 3, 4, 5, or 6 in which the salt is either a formate or an oxalate.

10. A process as claimed in claim 1, 2, 3, 4, 5, or 6 in which the salt is a nitrate.

11. A process as claimed in claim 1, 2, 3, 4, 5, or 6 in which the concentration of the solution of the salt is in excess of a 2 molar solution.

12. A process as claimed in claim 1, 2, 3, 4, 5, or 6 in which prior to contacting the crystalline silicate with the aqueous solution of a metal cation, it is put into the H-form.

* * * * *